United States Patent
Guiffray

(10) Patent No.: US 6,425,499 B1
(45) Date of Patent: Jul. 30, 2002

(54) FLUID PRODUCT SPRAYING DEVICE

(75) Inventor: Jean-Louis Guiffray, Petit Couronne (FR)

(73) Assignee: Valois S.A., Le Neubourg (FR)

( * ) Notice: Subject to any disclaimer, the term of this patent is extended or adjusted under 35 U.S.C. 154(b) by 0 days.

(21) Appl. No.: 09/582,620

(22) PCT Filed: Dec. 18, 1998

(86) PCT No.: PCT/FR98/02792

§ 371 (c)(1),
(2), (4) Date: Nov. 27, 2000

(87) PCT Pub. No.: WO99/34853

PCT Pub. Date: Jul. 15, 1999

(30) Foreign Application Priority Data

Dec. 31, 1997 (FR) ............................................. 97/16770

(51) Int. Cl.[7] ............................ B67D 5/52; A61M 37/00
(52) U.S. Cl. .......................... 222/137; 141/107; 604/89; 604/91
(58) Field of Search ............................. 604/82, 84, 89, 604/91; 222/137; 141/107

(56) References Cited

U.S. PATENT DOCUMENTS

| | | |
|---|---|---|
| 3,946,732 A | 3/1976 | Hurscham |
| 5,380,281 A | 1/1995 | Tomellini et al. ............. 604/85 |
| 5,569,191 A | 10/1996 | Meyer ........................ 604/82 |
| 5,569,193 A * | 10/1996 | Hofstetter et al. ........ 604/91 X |
| 5,637,087 A * | 6/1997 | O'Neil ......................... 604/82 |

FOREIGN PATENT DOCUMENTS

| | | |
|---|---|---|
| EP | 753 354 | 1/1997 |
| WO | WO 96/24439 | 8/1996 |

* cited by examiner

*Primary Examiner*—William Wayner
(74) *Attorney, Agent, or Firm*—Sughrue Mion, PLLC

(57) ABSTRACT

A fluid spray device comprising an outlet channel (120) terminating in a spray orifice (125), a first tank (110) containing a first substance, a second tank (210) containing a second substance, said two tanks (110, 210) being interconnected by a passage (160, 260) and prior to actuation of the device, being separated from each other in leakproof manner by sealing means (115, 215) disposed in said passage (160, 260), mixer means (130, 135; 235) being provided to open said passage (160, 260) and to mix together the two substances before they are dispensed, and dispenser means (235, 135) being provided for dispensing said mixture, the device being characterized in that said sealing means comprise at least one ball (115, 215) adapted to be expelled from the passage (160, 260) by said mixer means (130, 135; 235), said mixer means comprising a first piston (135; 235) slidably received in one of the tanks (110; 210) to transfer one of the substances from its tank (110; 210) into the other tank (210; 110), said dispenser means including a second piston (235; 135) slidably received in the other tank (210; 110) for dispensing the mixture of the two substances via the outlet channel (120).

11 Claims, 5 Drawing Sheets

FLUID PRODUCT SPRAYING DEVICE

The present invention relates to a device for dispensing a fluid, and more particularly a device for spraying a solution made up of a liquid and a powder that are mixed together at the last moment by the patient.

The invention relates more particularly to devices for dispensing a small number of doses, and preferably single-dose devices or two-dose devices.

Certain substances, and more particularly pharmaceuticals, can be highly unstable in solution over time and/or can require special storage conditions which can be awkward. In particular, they can be subject to oxidation, to hydrolysis, or to other kinds of spoiling which affect the quality and the effectiveness of the substance. One way of increasing lifetime and of avoiding problems associated with the chemical instabilities of such compounds and/or with storage conditions is to store them in the form of a powder and then make up a solution with a solvent immediately before administering the substance. This type of device is particularly suitable for treatment via the nose.

Documents EP-0 606 672 and EP-0 562 943 disclose devices each having a tank filled with liquid, a tank filled with powder, and a pump for dispensing a solution made by mixing those two substances. Prior to use, the powder is mixed with the liquid and then the liquid is dispensed in selective manner by means of the pump. Those devices present various drawbacks. Their structure does not enable the powder tank and the liquid tank to be filled and/or stored separately, thus making it impossible in particular to use freeze-drying for the powder tank. Unfortunately, in particular for devices that are to deliver a small number of doses, the accuracy of dosage can be considerably improved by filling the powder tank with a pre-dosed liquid solution and then freeze-drying the tank of solution. The fact that the two tanks cannot be stored separately also constitutes a drawback from the point of view of storing the device prior to use.

Certain documents, e.g. U.S. Pat. No. 3,946,743, U.S. Pat. No. 5,380,281, and U.S. Pat. No. 5,569,191 disclose dispenser devices such as syringes that are suitable for mixing together a powder and a liquid prior to dispensing the mixture. In those documents, the mixing process is implemented by means of a needle which pierces the stopper(s) closing the tanks in order to put them into communication. That implementation suffers from the drawback that while the membrane or gasket is being pierced, particles of the material constituting the membrane or the gasket run the risk of becoming mixed in with the fluid that is to be dispensed. This can pollute or contaminate the substance or can block the outlet channel during dispensing.

An object of the present invention is to provide a device for dispensing a fluid which does not suffer from the above drawbacks.

Another object of the present invention is to provide a device for dispensing a fluid which is simple and of low cost to manufacture and use.

Another object of the present invention is to provide such a device for spraying a solution that is made up extemporaneously, where the powder tank is made, filled, and/or stored separately from the liquid tank. In particular, an object of the present invention is to provide such a device which makes it possible to determine the dose in the powder tank by freeze-drying a pre-dosed liquid solution.

Another object of the present invention is to provide a device for dispensing a fluid in which a full dose of substance is dispensed on each actuation by proper spraying, in particular with nasal type uses.

A further object of the invention is to provide a device for spraying a fluid obtained by previously mixing together two different substances, in which the mixing process avoids any risk of the fluid for spraying becoming polluted or contaminated, and avoids any risk of the outlet channel becoming blocked.

The present invention thus provides a fluid spray device comprising an outlet channel terminating in a spray orifice, a first tank containing a first substance, a second tank containing a second substance, said two tanks being interconnected by a passage and, prior to actuation of the device, being separated from each other in leakproof manner by sealing means disposed in said passage, mixer means being provided to open said passage and to mix together the two substances before they are dispensed, and dispenser means being provided for dispensing said mixture, said mixer means comprising a first piston slidably received in one of the tanks to transfer one of the substances from its tank into the other tank, said dispenser means including a second piston slidably received in the other tank for dispensing the mixture of the two substances via the outlet channel, the device being characterized in that said sealing means comprise at least one ball adapted to be expelled from the passage by the pressure created in one of the tanks when said first piston is actuated.

Advantageously, said mixer means comprise a hollow rod secured to the first piston and adapted to penetrate into said passage to expel the balls and, after the two substances have been mixed together, extending to the second tank in such a manner that said hollow rod forms the inlet end of the outlet channel.

Preferably, said mixer means are actuated independently of said dispenser means.

In a preferred variant, said dispenser means are adapted to dispense the entire mixture of the two substances in a single actuation.

In another variant, said dispenser means include or co-operate with stop means for subdividing the mixture of the two substances into a plurality of doses, one dose being dispensed on each actuation.

In an advantageous embodiment of the invention, the device comprises two independent subassemblies, the first subassembly having the outlet channel, the first tank, and one of the pistons, and the second subassembly having the second tank and the other piston, connection means being provided for connecting the two subassemblies together.

Advantageously, each of the first and second tanks has a respective ball expelled during actuation of the mixer means.

In another embodiment of the invention, the mixer means comprise the piston disposed in the second tank, actuation of said piston creating sufficient pressure in the second tank to expel the ball from the passage into the inside of the first tank and to transfer the substance contained in the second tank into the first tank to mix therein with the other substance, the dispenser means including the piston disposed in the first tank, with actuation thereof serving to dispense the mixture.

Preferably, one of the substances is a liquid and the other substance is a powder, mixing being performed extemporaneously by transferring the liquid into the tank containing the powder.

Advantageously, said first tank contains a solvent and said second tank contains a powder, or vice versa.

Preferably, said powder is a pre-dosed liquid solution that has subsequently being freeze-dried.

Other characteristics and advantages of the present invention will appear on reading the following detailed description given by way of non-limiting example and with reference to the accompanying drawings, in which.

Figure 1:
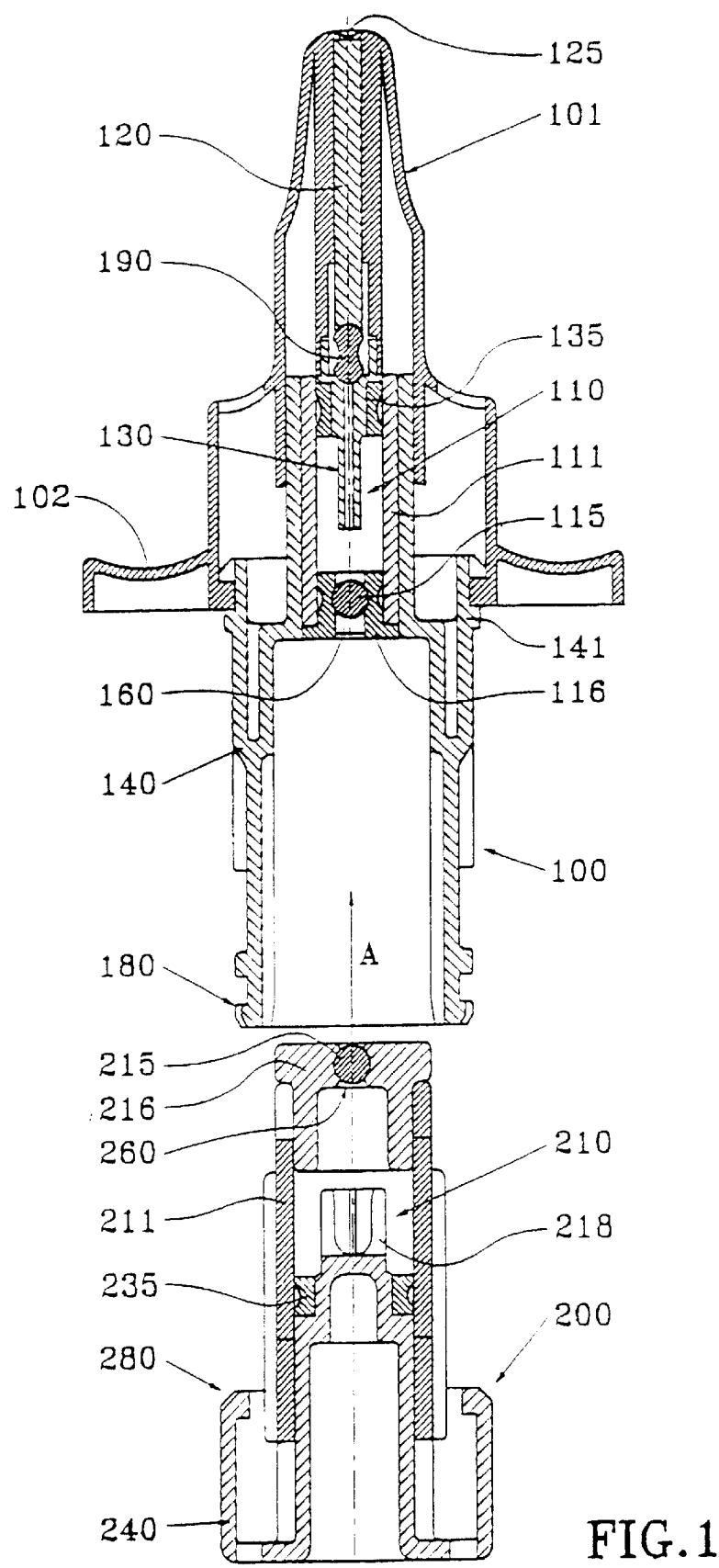
FIG. 1 is a diagrammatic section view of an advantageous embodiment of the invention, prior to the device being assembled.

FIGS. 1 to 4 show an advantageous embodiment in which the dispenser device is constituted by two subassemblies which are separate and which can therefore be manufactured, filled, and stored separately, ready to be assembled together when the device is to be used. It should be understood that the present invention can also apply to devices made in non-separable manner, as shown by way of example in FIG. 5.

Likewise, the device shown in the drawings is more particularly suitable for nasal type use. The pushbutton therefore has a nasal endpiece 101 that penetrates into a nostril and a bearing zone 102 that enables the device to be actuated. This outside shape for a nasal pushbutton is well known and is therefore not described in greater detail below. Naturally, the invention is applicable to any type of device and it is not limited to nasal type uses.

In the invention, the device has a first tank 110 which contains a first substance, and a second tank 210 which contains a second substance, the two substances being intended for mixing together immediately prior to being dispensed so as to avoid spoiling of the mixture. In particular, one of the substances is a liquid and the other substance is a powder, such that the mixture is a solution which can be sprayed finely through the outlet orifice 125 of the pushbutton.

In the embodiment of FIGS. 1 to 4, the device is constituted by two subassemblies. The first subassembly 100 incorporates the first tank 110 and the outlet channel 120 which opens out into the outlet orifice 125 and which is surrounded by the nasal endpiece 101 that extends down to the bearing zone 102 of the pushbutton. The outlet channel, 120 is preferably substantially filled by an internal nozzle which serves to minimize the dead volume and thus to ensure good spraying when the device is actuated. Advantageously, the internal nozzle extends over a major fraction of the nasal endpiece 101 to a resilient shutter 190 provided in the outlet channel and forming an outlet check valve. The first tank 110 advantageously includes a glass tube 111 which makes it possible to guarantee that the liquid can be stored over time. The tank 110 is closed firstly by a wall or a shutter element 116 which has a passage 160 into which sealing means 115 is inserted, e.g. a ball, so as to close the tank 110 after it has been filled. At its opposite end, in the invention, the tank has a piston 135 capable of sliding in leakproof manner inside the tank, said piston forming a portion of the mixer means used for mixing the two substances of the device, as explained below.

The first subassembly 100 also has a body 140 secured to the tank 110 and connected to the pushbutton 101, 102 in such a manner that the pushbutton can slide relative to said body 140, thereby displacing said piston 135 inside the tank 110. The body 140 preferably includes abutment means 141 which prevent any displacement of the pushbutton relative to the body 140 in a first position, referred to as a "waiting position", and which enable such displacement to occur in a second position, referred to a as a "pre-mixing" position. In particular, the pushbutton is moved into said pre-mixing position by turning the pushbutton on the body 140. At its opposite end, the body 140 has connection means 180 adapted to make a connection with the second subassembly 200 of the device, as described below.

The second subassembly 200 of the device includes the second tank 210 containing the second substance, which is preferably a powder. This second tank is closed at one end by a shutter wall or element 216 which has a passage 260 that is closed by a sealing element 215, preferably a ball. At its opposite end, the tank 210 has a piston 235 capable of sliding in leakproof manner in the second tank 210 so as to dispense the substance contained therein. The piston 235 is urged to move by a body 240 which is actuated by the user in order to dispense the substance. This body 240 can therefore slide relative to said first tank 210 and advantageously includes connection means 280 for connecting to the connection means 180 of the first subassembly 100. This connection of the two subassemblies is advantageously by snap-fastening.

Figure 2:
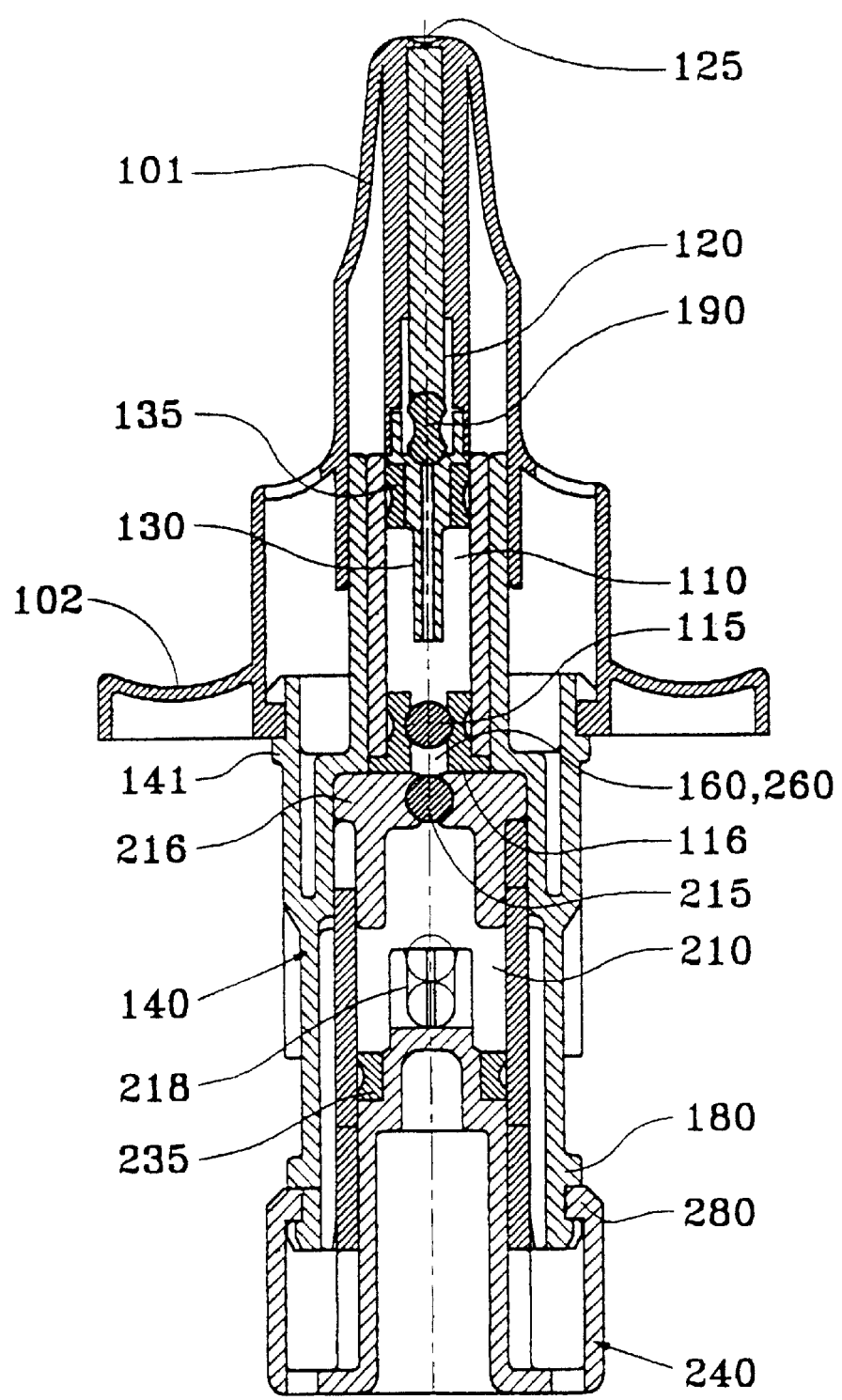
FIG. 2 is a view similar to FIG. 1, after the device has been assembled but before the substances have been mixed together.

With reference to FIGS. 1 and 2, the way in which the two subassemblies are connected together in shown diagrammatically. Thus, the first tank 110 is filled with a liquid substance and is then closed by the shutter element 116 and a ball 115, while separately the second tank 210 is filled with a powder and then closed by the shutter element 216 and a ball 215, such that the two subassemblies can be stored separately. The respective shutter means 115, 116 and 215, 216 can naturally be implemented in any appropriate manner. On being assembled together, the second subassembly 200 is inserted in the direction of arrow A into the inside of the skirt of the body 140 of the first subassembly 100. When the shutter wall or element 216 of the second subassembly 200 comes into abutment against the shutter wall or element 116 of the first subassembly 100, the connection means 180 and 280 of the two subassemblies snap together to hold the two subassemblies together as shown in FIG. 2. In addition, the passages 160 and 260 are in alignment to form a passage connecting the first tank 110 to the second tank 210, said passage being closed by the two sealing means, i.e. the two balls 115 and 215 in the example shown.

As can be seen in the figures, in the preferred embodiment of the invention, the second tank 210 has receiver means 218 for receiving said sealing means 115 and 215 after they have been opened, i.e. after they have been moved away from their shutting positions by the mixer means. In FIG. 2, the device is thus shown in its waiting position, with the two subassemblies connected together.

Figure 3:
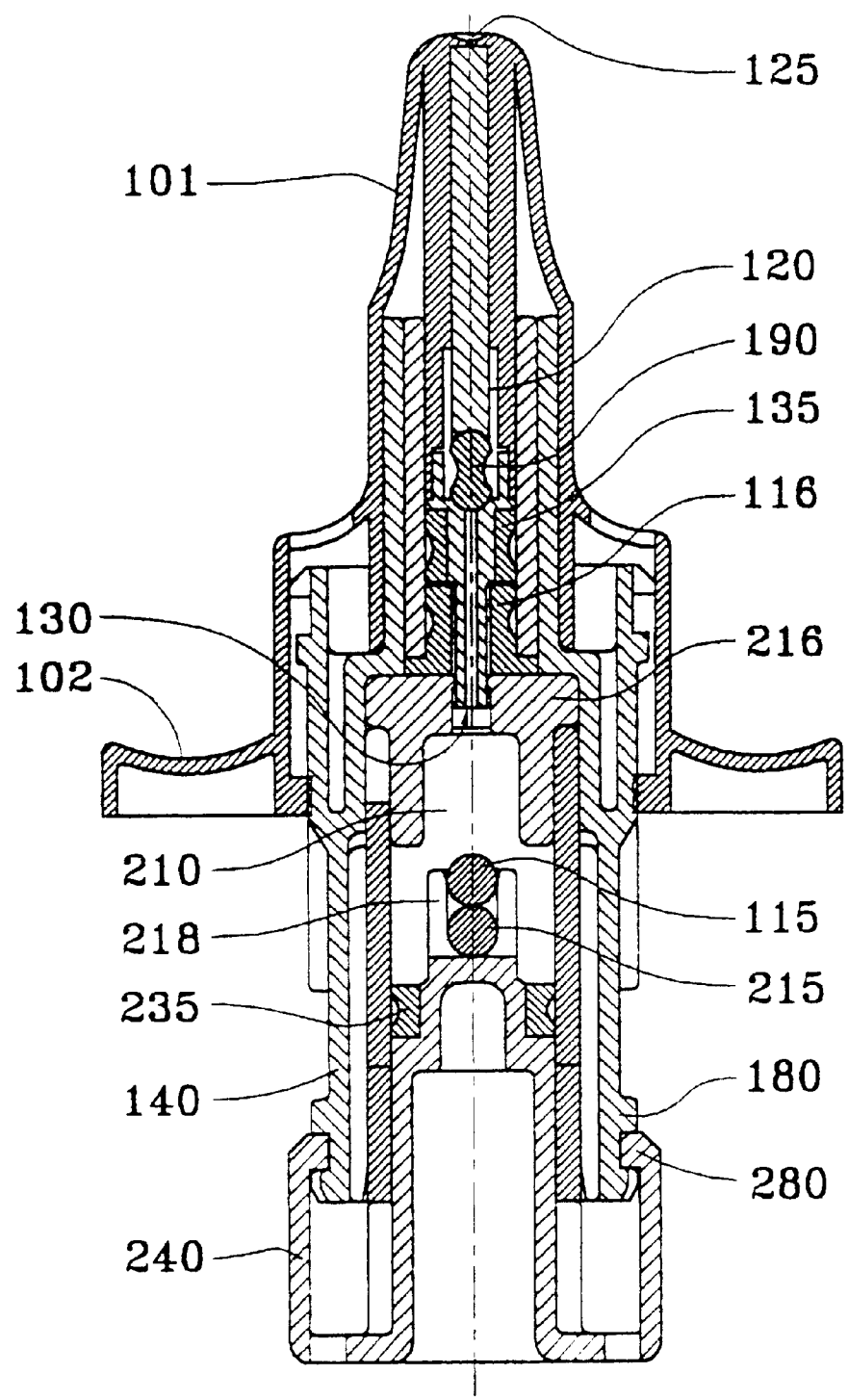
FIG. 3 is a view similar to FIG. 2, after the substances have been mixed together but before the mixture of substances has been dispensed.

Immediately before the user desires to use the device, the two substances should be mixed together. To do so, the mixer means provided in the first subassembly 100 preferably include a hollow rod 130 which forms a portion of the outlet channel 120 and which is secured to the first piston 135 that slides in the first tank 110. Advantageously, this hollow rod 130 is suitable for penetrating into the passage 160, 260 formed between the two tanks, and is adapted to expel the sealing means 115 and 215 from their closure positions. Thus, when the user desires to mix the substances, the pushbutton should be turned on the body 140 of the device into its premixing position, and then pressure should be applied to the pushbutton so as to cause the body 140 to move relative to the pushbutton. During this displacement, the piston 135 slides in the first tank 110 and the end of the rod 130 expels first the ball 115 and then the ball 215 from their closure positions, thereby opening the passage 160, 260 between the two tanks. Since the passage is open, the liquid contained in the first tank 110 is transferred into the second tank 210 so as to mix with the powder contained therein. After relative displacement between the pushbutton and the body 140 has been completed, all of the liquid substance has been transferred into the second tank and the device is in a "pre-dispensing" position. The rod 130 preferably extends as far as the inlet to the second tank 210, thereby forming the inlet to the outlet channel 120. As shown in FIG. 3, in the pre-dispensing position after mixing has taken place, the two balls 115 and 215 are received in the receiver means 218 of the second tank 210, and the end of the hollow rod 130 is situated in the immediate vicinity of the inlet to the tank 210. Thus, dead volume is minimized, in particular because the first tank 110 has completely disappeared in the position shown in FIG. 3. Furthermore, the use of sealing means such as balls avoids the drawbacks that exist in prior devices which made use of membranes suitable for piercing by a needle. In a variant, the hollow needle 130 can be omitted, with the balls being expelled from the passage 160, 260 by the pressure that is created in the first tank 110 when the first piston 135 is actuated.

In the pre-dispensing position shown in FIG. 3, the device is ready for use. When the user seeks to dispense the substance contained in the second tank 210, pressure should be applied to the pushbutton and the body 240 so that relative axial displacement occurs between the body 240 and the body 140, thereby causing the piston 235 to slide in leakproof manner inside the second tank 210, thus expelling the contents of said tank. The user should preferably turn the body 240 relative to the body 140 in order to move the connection means 180, 280 from a position in which axial displacement is prevented to a position in which the connection means co-operate in such a manner as to allow axial displacement to occur of the two bodies 140 and 240 relative to each other.

When the device is a single-dose device, one actuation expels the entire contents of the second tank 210. Nevertheless, provision can equally well be made for two or more doses by providing abutment means (not shown) e.g. disposed on the body 140 to form dose-stops, with the contents of the tank 210 thus being subdivided into a plurality of doses. To overcome said abutment means and thus deliver subsequent doses, the body 240 should advantageously be turned again relative to the body 140 so as to allow the piston 235 to continue its stroke through the second tank 210.

Figure 4:
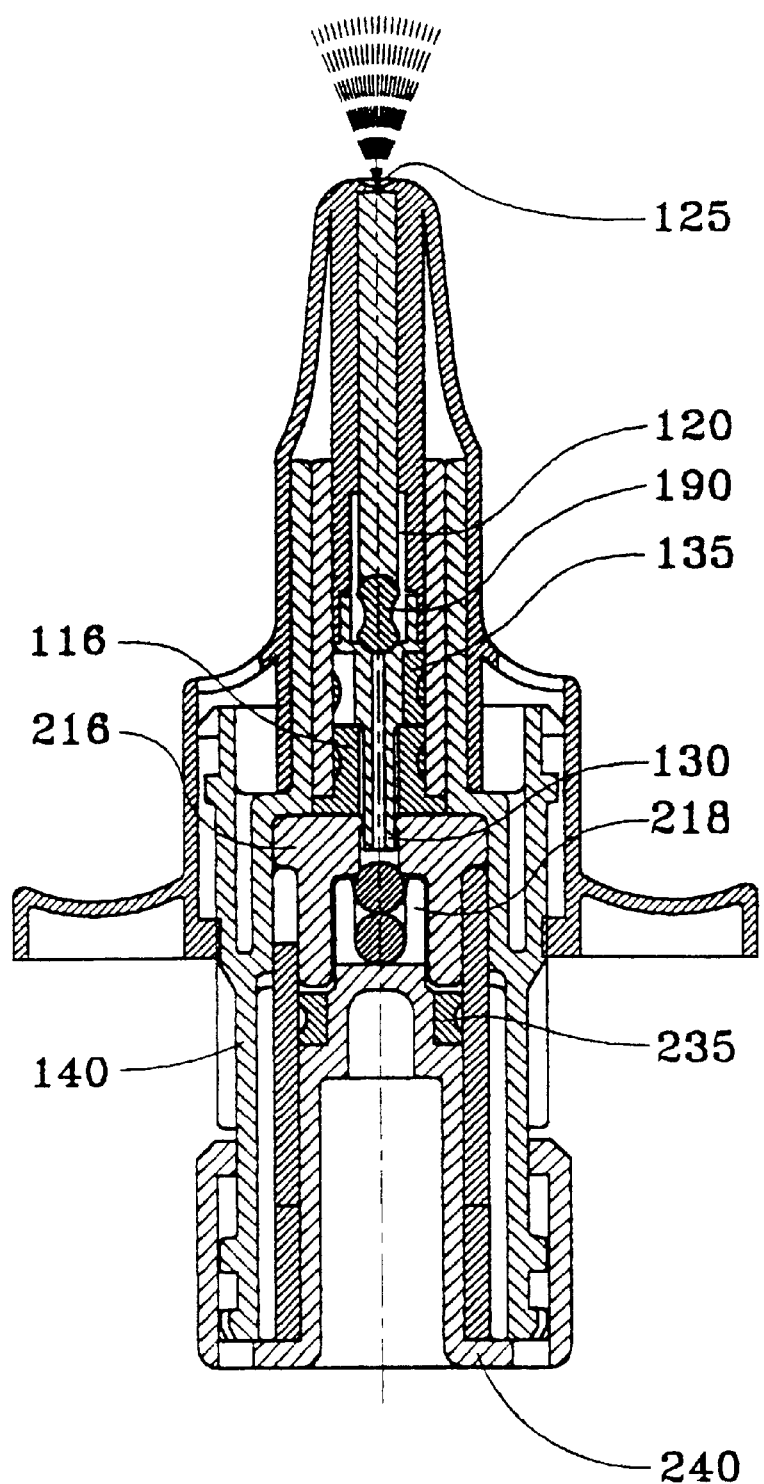
FIG. 4 is a view similar to FIG. 3, after the mixture of substances has been dispensed.

In the end-of-expulsion position shown in FIG. 4, it can be seen that the second tank 210 has likewise completely disappeared, with the inlet of the hollow rod 130 being situated in the immediate vicinity of the sealing means 115, 215 received in the receiver means 218 of the second tank, such that the dead volume is almost zero, thereby guaranteeing that nearly all of the substance contained in the second tank has been expelled.

The description above is given with reference to an advantageous embodiment in which the device is constituted by two separate subassemblies. Nevertheless, it is possible to envisage making the device as a single unit. Under such circumstances, a single sealing means suffices in the passage between the two tanks, however the general operation of the device is similar to that described above.

Figure 5:
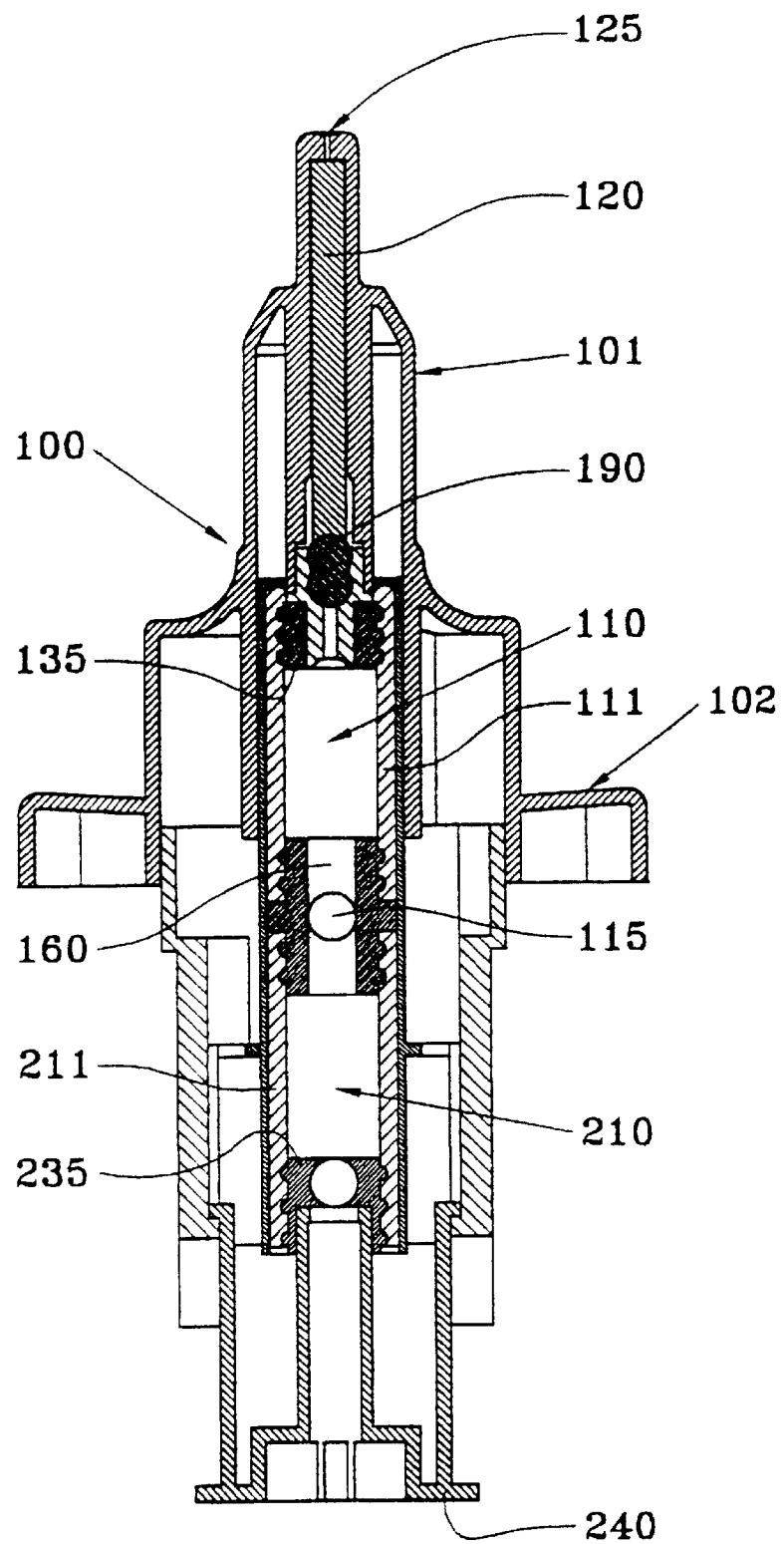
FIG. 5 is a diagrammatic section view of another embodiment of the invention.

FIG. 5 shows such a variant embodiment. The device has two tanks 110 and 210 each containing a respective piston 135 or 235, and separated from each other by a passage 160 that is closed in sealed manner by a ball 115. In this variant, the "top" tank 110 advantageously contains a powder while the "bottom" tank advantageously contains a solvent (with the terms "top" and "bottom" relating to the position of the device as shown in FIG. 5). In this case, the mixer means comprise the piston 235 actuated by applying pressure to the body 240. This actuation raises the pressure in the second tank 210 which expels the ball 115 from the passage 160 into the first tank 110. The stroke of the piston 235 then transfers the liquid to the first tank 110 where the two substances are mixed together. The mixture is then dispensed by actuating the first piston 135. In this variant, both tanks form parts of a common subassembly and they are therefore packaged and stored together. The advantage of this variant lies in its simplicity, its small number of component parts, and its reliability when actuated.

Nevertheless, the embodiment shown in FIGS. 1 to 4 made up of two subassemblies also presents significant advantages. Thus, the manufacture, filling, and/or storage of the two subassemblies can take place in completely separate manner. This makes it possible to save space, greatly facilitates the filling of each of the two tanks, and above all makes it possible to use freeze-drying in order to form the powder in the second tank 210. In order to improve dose accuracy, the second tank 210 is preferably filled with a pre-dosed liquid solution, then the closure plug 216 with its ball 215 is prepositioned on said tank 210, but without closing it. Thereafter, freeze-drying is performed, thereby leaving an accurately measured quantity of powder inside the tank 210, and finally the plug is pushed home so as to close said tank 210 in sealed manner. Clearly this preferred embodiment using freeze-drying is not essential, and the second tank 210 could be prefilled with a desired quantity of powder.

Another advantage of the device in either of the two embodiments described above is that it makes it possible to provide a compact device which is reliable for the user by preventing any undesired actuation because it is essential to turn the pushbutton relative to a first body (e.g. the body 140 in the example of FIGS. 1 to 4) in order to perform mixing, and of said first body relative to a second body (e.g. the body 240 in the example of FIG. 1 to 4) in order to dispense said mixture. The same applies when the contents of the tank to be dispensed is to be subdivided into a plurality of doses. Any accidental or unwanted use is thus prevented.

Other variants of the device can be envisaged without thereby going beyond the ambit of the present invention. Thus, the shutter 190 provided in the outlet channel 120 can be made in any manner. In the example shown in the figures, it is constituted by a piece of elastomer or rubber that deforms under the pressure exerted by the substance. The shutter could also be disposed in the immediate vicinity of the outlet orifice. Similarly, the general outside shape of the device could be different. The connection means between the pushbutton and the body 140 and between the body 140 and the body 240 could also be made in other ways. Advantageously, it is desirable for said connection means to perform said safety function by preventing actuation in a given angular position while allowing actuation in a different angular position. Furthermore, the connection means 180 and 280 between the body 140 of the first subassembly and the body 240 of the second subassembly can be implemented in such a way that when in the position that allows said two bodies to move in relative axial displacement, a small rib releases such axial displacement only after a predetermined force has been applied to the device, so that energy is stored in the hand of the user, thereby guaranteeing that one dose is expelled in full on each actuation.

What is claimed is:

1. A fluid spray device comprising an outlet channel (120) terminating in a spray orifice (125), a first tank (110) containing a first substance, a second tank (210) containing a second substance, said two tanks (110, 210) being interconnected by a passage (160, 260) and, prior to actuation of the device, being separated from each other in leakproof manner by sealing means (115, 215) disposed in said passage (160, 260), mixer means (130, 135; 235) being provided to open said passage (160, 260) and to mix together the two substances before they are dispensed, and dispenser means (235, 135) being provided for dispensing said mixture, said mixer means comprising a first piston (135; 235) slidably received in one of the tanks (110; 210) to transfer one of the substances from its tank (110; 210) into the other tank (210; 110), said dispenser means including a second piston (235; 135) slidably received in the other tank (210; 110) for dispensing the mixture of the two substances via the outlet channel (120), the device being characterized in that said sealing means comprise at least one ball (115, 215) adapted to be expelled from the passage (160, 260) by the pressure created in one/of the tanks (110; 210) when said first piston (135; 235) is actuated.

2. A device according to claim 1, in which said mixer means comprise a hollow rod (130) secured to the first piston (135) and adapted to penetrate into said passage (160, 260) to expel the balls (115, 215) and, after the two substances have been mixed together, extending to the second tank (210) in such a manner that said hollow rod (130) forms the inlet end of the outlet channel (120).

3. A device according to claim 1 or 2, in which said mixer means (130, 135; 235) are actuated independently of said dispenser means (235; 135).

4. A device according to claim 1, in which said dispenser means (235; 135) are adapted to dispense the entire mixture of the two substances in a single actuation.

5. A device according to claim 1, in which said dispenser means (235; 135) include or co-operate with stop means for subdividing the mixture of the two substances into a plurality of doses, one dose being dispensed on each actuation.

6. A device according to claim 1, in which the device comprises two independent subassemblies (100, 200), the first subassembly (100) having the outlet channel (120), the first tank (110), and one of the pistons (135), and the second subassembly (200) having the second tank (210) and the other piston (235), connection means (180, 280) being provided for connecting the two subassemblies (100, 200) together.

7. A device according to claim 6, in which each of the first and second tanks (110, 210) has a respective ball (115, 215) expelled during actuation of the mixer means.

8. A device according to claim 1, in which the mixer means comprise the piston (235) disposed in the second tank (210), actuation of said piston (235) creating sufficient pressure in the second tank (210) to expel the ball (115) from the passage (160) into the inside of the first tank (110) and to transfer the substance contained in the second tank (210) into the first tank (110) to mix therein with the other substance, the dispenser means including the piston (135) disposed in the first tank (110), with actuation thereof serving to dispense the mixture.

9. A device according to claim 1, in which one of the substances is a liquid and the other substance is a powder, mixing being performed extemporaneously by transferring the liquid into the tank containing the powder.

10. A device according to claim 1, in which said first tank (110) contains a solvent and said second tank (210) contains a powder, or vice versa.

11. A device according to claim 9, in which said powder is a pre-dosed liquid solution that has subsequently being freeze-dried.

* * * * *